US008853845B2

(12) United States Patent
Souriau et al.

(10) Patent No.: US 8,853,845 B2
(45) Date of Patent: Oct. 7, 2014

(54) COMPONENT WITH ENCAPSULATED ACTIVE ELEMENT AND IMPLANTABLE MEDICAL ADVICE INCORPORATING SUCH A COMPONENT

(71) Applicants: Commissariat a l'energie atomique et aux ene alt, Paris (FR); Sorin CRM S.A.S., Clamart Cedex (FR)

(72) Inventors: Jean-Charles Souriau, Saint Egreve (FR); Guy-Michel Parat, Claix (FR); Renzo Dal Molin, Chatillon (FR)

(73) Assignees: Commissariat a l'energie atomique et aux energies alternatives, Paris (FR); Sorin CRM S.A.S., Clamart (FR)

( * ) Notice: Subject to any disclaimer, the term of this patent is extended or adjusted under 35 U.S.C. 154(b) by 0 days.

(21) Appl. No.: 13/845,926

(22) Filed: Mar. 18, 2013

(65) Prior Publication Data
US 2013/0296658 A1 Nov. 7, 2013

(30) Foreign Application Priority Data

May 3, 2012 (FR) ...................................... 12 54079

(51) Int. Cl.
*H01L 23/02* (2006.01)
*B81B 7/00* (2006.01)
*A61B 5/00* (2006.01)
*G01D 11/24* (2006.01)
*H01L 21/56* (2006.01)

(52) U.S. Cl.
CPC ................. *A61B 5/686* (2013.01); *B81B 7/007* (2013.01); *B81C 2203/0118* (2013.01); *G01D 11/245* (2013.01); *B81C 2203/0109* (2013.01); *H01L 21/56* (2013.01); *H01L 2224/48091* (2013.01); *B81B 2201/0214* (2013.01); *B81C 2203/0145* (2013.01); *H01L 2224/16225* (2013.01)
USPC ................... 257/678; 257/687; 257/E33.056; 257/E23.001; 257/E21.499

(58) Field of Classification Search
USPC .................. 257/678, 687, E33.056, E23.001, 257/E21.499
See application file for complete search history.

(56) References Cited

U.S. PATENT DOCUMENTS

| | | | |
|---|---|---|---|
| 4,023,562 A | 5/1977 | Hynecek et al. | |
| 5,832,207 A | 11/1998 | Little et al. | |
| 5,850,450 A | 12/1998 | Schweitzer et al. | |
| 5,998,858 A | 12/1999 | Little et al. | |
| 6,219,789 B1 | 4/2001 | Little et al. | |
| 2001/0011353 A1 | 8/2001 | Little et al. | |
| 2002/0115920 A1 | 8/2002 | Rich et al. | |
| 2008/0102096 A1 | 5/2008 | Molin et al. | |
| 2013/0293428 A1 | 11/2013 | Souriau et al. | |

FOREIGN PATENT DOCUMENTS

| | | |
|---|---|---|
| EP | 1 903 000 A2 | 3/2008 |
| EP | 1 903 000 A3 | 3/2008 |
| WO | WO 97/04377 | 2/1997 |

OTHER PUBLICATIONS

H. Grange, et al., "A Bi-Axis Accelerometer with a Chip Size Packaging Technology for a Pacemaker Application", LETI-CEA/Grenoble, France. In Proceeding of Solid-State Device Research Conference, 1998, Proceeding of the 28th European., 4 pages.

Jun Su Lee, et al., "A Cost-Effective MEMS Cavity Packaging Technology for Mass Production", IEEE Transactions on Advanced Packaging, vol. 32, No. 2, May 2009, pp. 453-460.

Rajen Chanchani, et al., "A New Wafer-Level Packaging Technology for MEMS with Hermetic Micro-Environment", Electronic Components and Technology Conference (ECTC), 2011, IEEE 61st., pp. 1604-1609.

Adam Schubring, et al., "Ceramic Package Solutions for MEMS Sensors", Electronics Manufacturing Technology Symposium, IEMT'07, 2007, 5 pages.

Tao Wang, et al., "Design and Realize of 3D Integration of a Pressure Sensor System with Through Silicon Via (TSV) Approach", Electronic Packaging Technology and High Density Packaging (ICEPT-HDP), 2011, 12th International Conference on., pp. 40-43.

Krystan Marquardt, et al., "Development of near hermetic silicon/glass cavities for packaging of integrated lithium micro batteries", Design Test, Integration & Packaging of MEMS/MOEMS, Apr. 1-3, 2009. Symposium on MEMS/MOEMS'09, 8 pages.

Yong-Seung Bang, et al., "Fabrication and Characterization of RF MEMS Package Based on LTCC Lid Substrate and Gold-Tin Eutectic Bonding", Solid State Sensors, Actuators and Microsystems Conference, 2007, Transducers 2007. International, pp. 2115-2118.

S.-H. Lee, et al., "A Generic Environment-Resistant Packaging Technology for MEMS", Solid State Sensors, Actuators and Microsystems Conference, 2007. Transducers 2007, International, pp. 335-338.

C. Ferrandon, et al, "Hermetic Wafer-Level Packaging development for RF MEMS switch", Electronic System-Integration Technology Conference (ESTC), 2010, pp. 1-6.

Yoshiaki Sugizaki, et al, "Novel Wafer-level CSP for Stacked MEMS/IC Dies with Hermetic Sealing", Electronic Components and Technology Conference, May 27-30, 2008, pp. 811-816.

Chiung-Wen Lin, et al., "THRU-Wafer Interconnect for SOI-MEMS 3D Wafer-Level Hermetic Packaging", Solid State Sensors, Actuators and Microsystems Conference, 2007. Transducers 2007, International, pp. 2111-2114.

Alain Phommahaxay, et al., VIA-Free Interconnection in Quasi-Hermetic Wafer-Level Packaging for RF-MEMS Applications and 3D Integration, Solid State Sensors, Actuators and Microsystems Conference, 2007. Transducers 2007, International, pp. 2063-2066.

Yuhan Cao, et al., "Wafer-Level Package With Simultaneous TSV Connection and Cavity Hermetic Sealing by Solder Bonding for MEMS Device", IEEE Transactions on Electronics Packaging Manufacturing, vol. 32, No. 3, Jul. 2009, pp. 125-132.

Dehui Xu, et al, "Wafer Level Vacuum Packaging of Micromachined Thermoelectric IR Sensors", IEEE Transactions on Advanced Packaging, vol. 33, No. 4, Nov. 2010, pp. 904-911.

Preliminary Search Report issued Dec. 17, 2012 in French Application No. 1254079 (With English Translation of Category of Cited Documents).

Brian Hindman, "Application Note 3808 What is an iButton?", URL http://pdfserv.maximintegrated .com/en/an/AN3808.pdf, Jun. 1, 2006, XP055047087, 5 pages.

*Primary Examiner* — Timor Karimy
(74) *Attorney, Agent, or Firm* — Oblon, Spivak, McClelland, Maier & Neustadt, L.L.P.

(57) ABSTRACT

A component including at least one active element hermetically encapsulated in a cavity formed between a support and a cover, in which the support and the cover are made from an electrically conductive material, and are insulated electrically from one another, and include a first electrical connection between the active element and the support, and a second electrical connection, separate from the first connection, between the active element and the cover, and in which:

the active element is securely attached to the support through a dielectric layer positioned between the support and the active element, and between the support and the cover;

the second electrical connection includes a second portion of electrically conductive material electrically connected to the cover, positioned on the dielectric layer and electrically in contact with an electrically conductive sealing bead providing hermetic secure attachment of the cover to the support.

11 Claims, 7 Drawing Sheets

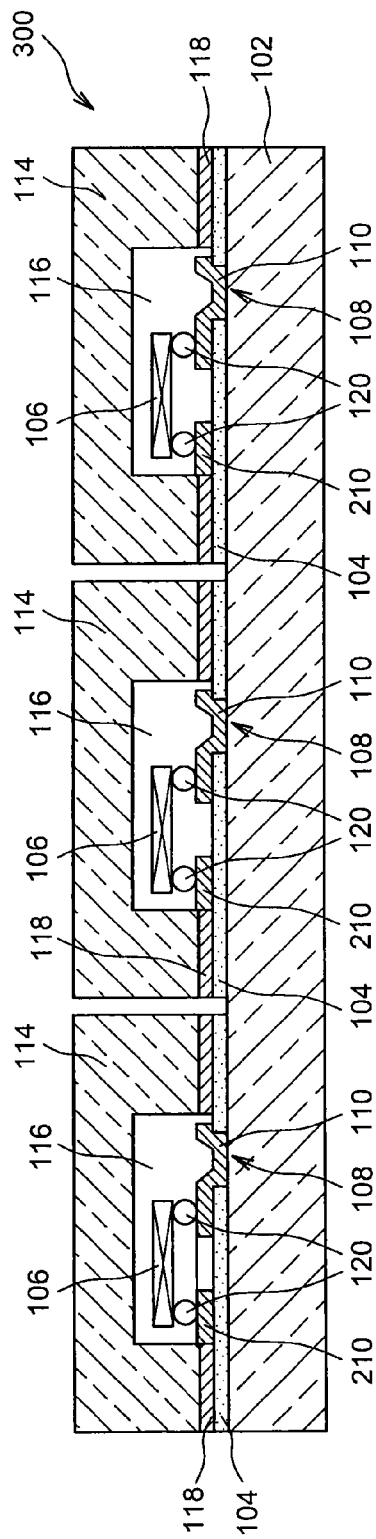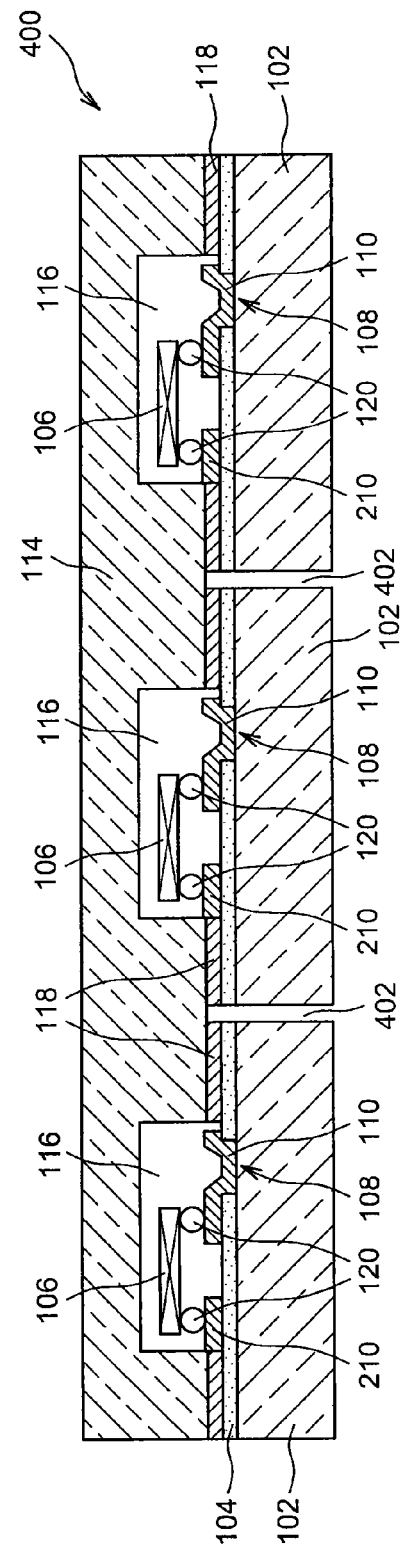

COMPONENT WITH ENCAPSULATED ACTIVE ELEMENT AND IMPLANTABLE MEDICAL ADVICE INCORPORATING SUCH A COMPONENT

TECHNICAL FIELD

The application relates to a component with an encapsulated active element including at least two electrical connections, which can be immersed in particular in media which are hostile for electronics, for example, if the component is intended to be implanted in a body, or a part of a body, whether human or animal. The component may be biocompatible, or made biocompatible for the field of active medical devices as defined by directive 93/42/CEE of 14 Jun. 1993, and notably that of active implantable medical devices, as defined by directive 90/385/CEE of 20 Jun. 1990. The application relates to a component, and notably a biocompatible component, a method for producing such a component, and also an implantable medical device including such a component which has been made biocompatible.

The invention may be advantageously used for the production of active medical devices such as:
- devices for supervising cardiac activity and for generating stimulation pulses, resynchronisation pulses, defibrillation pulses and/or cardioversion pulses in the event of detection of cardiac disorders,
- neurological devices,
- pumps for diffusing medical substances,
- cochlear implants,
- implanted biological sensors,
- pH measuring devices,
- intracorporeal impedances (measurement of transpulmonary or intracardial impedance).

STATE OF THE PRIOR ART

An active implantable medical device includes one or more active elements, such as sensors allowing one or more physiological parameters to be measured and/or various functions of the medical device to be controlled.

The sensors can be incorporated in a probe which is itself connected to a generating unit of the device. The sensors are, for example, blood pressure sensors or endocardial acceleration sensors installed at the distal end of an intracavitary probe intended to be introduced into the myocardium and connected to the unit of a simulator or defibrillator. More generally, these active elements can also be micro-electromechanical systems (MEMS), nano-electromechanical systems (NEMS) or again integrated electronics circuits, for example of the ASIC or FPGA type, implementing signal amplification functions, filtering functions, etc.

In order to be able to be implanted in human or animal body, the active elements are coated in a biocompatible material (which is notably sealed), i.e. a material which is completely inert with regard to surrounding bodily tissues and fluids, and which does not deteriorate despite prolonged contact with the surrounding biological environment.

Certain standards also require that the packaging of the active elements is produced with a twin level of protection, having biocompatibility not only of the outer coating, but also biocompatibility of the coated element (in which the active element is contained), in order to provide protection even in the event of indirect contact, for example due to diffusion through the coating, between the coated element and the surrounding medium, or again in the event of damage, injury or cracking of the coating.

To satisfy such standards, document EP 1 903 000 A2 proposes the production of an active element on a substrate of silicon doped with boron or borosilicate, followed by encapsulation of the active element in a cavity made by transferring and hermetically sealing a cover, also consisting of silicon or borosilicate, on the substrate. To access the active element electrically, electrical connections between the active element and the outside of the cavity are formed by conductive vias produced through the substrate, where the ends of these vias are connected to electrical contact terminals produced either side of the substrate (i.e. both in the cavity, in order to be connected electrically to the active element, and on the rear face of the substrate).

The produced medical device must be hermetic, i.e. resistant not only to the penetration of liquids (sealing), but also to that of gases, which presupposes a rate of leakage with regard to the cavity in the medical device which is completely controlled and infinitesimal.

A means to measure the absence or presence of leaks consists in measuring a deflection of the membrane of the cover according to a pressure differential between the interior of the cavity and the external environment. Bearing in mind the material of the membrane of the cover, its dimensions and the pressure differential at its terminals, the membrane's deflection can be calculated. Conversely, bearing in mind the membrane's external pressure (dimensions and material), its internal pressure can be deduced.

The solution proposed by document EP 1 903 000 A2 enables these standards relative to double protection of the active elements intended to be implanted to be met. However, this solution implies the production of a stack (substrate+cover) made of silicon or quartz incorporating both cavities and through vias in the presence of a cover which is machined and sealed hermetically in the substrate, something which is complex and expensive to implement.

In addition, in fields other than the medical field, it is known to package one or more active elements (such as inertial, acoustic, temperature, radiation, etc. sensors) in closed cavities. The electric connection of these active elements is accomplished from the interior to the exterior of the cavity by TSVs (Through Silicon Vias). This contact technology requires, as before, a substantial number of steps, and this method is therefore expensive to implement.

DESCRIPTION OF THE INVENTION

Thus there is a need to propose a component incorporating one or more active and/or passive elements encapsulated in a cavity which are able to be contacted electrically from the outside of the cavity, and which is less complex and less expensive to produce than the components of the prior art.

One embodiment may notably be a biocompatible component able to be implanted in a body, or in a part of a body, whether human or animal, satisfying the requirements of protection of the active element or elements of the component, the exterior at least of which is biocompatible.

To this end, a component is proposed including at least one active element hermetically encapsulated in at least one cavity formed between at least one support and at least one cover, in which the support and the cover are made from at least one electrically conductive material, and are electrically insulated from one another, and include a first electrical connection between the active element and the support, and a second electrical connection, separate from the first electrical connection, between the active element and the cover.

One embodiment relates to a component including at least one active element hermetically encapsulated in at least one cavity formed between at least one support and at least one cover, in which the support and the cover are made from at least one electrically conductive material, and are electrically insulated from one another, and include a first electrical connection between the active element and the support, and a second electrical connection, separate from the first electrical connection, between the active element and the cover, and in which:

the active element is securely attached to the support through at least one dielectric layer positioned between the support and the active element, and between the support and the cover;

the second electrical connection includes at least one second portion of electrically conductive material electrically connected to the cover, positioned on the dielectric layer and electrically in contact with an electrically conductive sealing bead providing hermetic secure attachment of the cover to the support.

With such a component, all, or almost all, of the outer surface of the support and of the cover can thus be used to form electrical means of access to the encapsulated active element. In addition, with such a component, there is no requirement to produce conductive vias through the support and/or the cover, given that the entire electrically conductive support and the entire electrically conductive cover form electrical connections with the active element.

A biocompatible component is also described which can be implanted in at least one part of a human or animal body, including at least one active element hermetically encapsulated in at least one cavity formed between at least one support and at least one cover, in which the support and the cover are made from an electrically conductive material, where the active element is electrically connected to the support and to the cover by two separate electrical connections.

A biocompatible component is also proposed which is able to be implanted in at least one part of a human or animal body, including at least one active element hermetically encapsulated in at least one cavity formed between at least one support and at least one cover, in which the support and the cover each have at least one layer completely, or fully, consisting of electrically conductive material, where the active element is electrically connected to the layers consisting of electrically conductive material of the support and of the cover.

All, or almost all, of the surface of the front face and of the rear face of the component, i.e. the entirety or almost the entirety of the surface of the front face of the cover and of the rear face of the support, may be electrically conductive. The entirety, or almost the entirety, of the surface of the lateral faces of the cover and of the support may also be electrically conductive.

The active element may include at least one integrated electronic circuit and/or one device of the MEMS/NEMS type and/or one sensor measuring at least one physiological parameter. The component may include, generally, any type of active element, and possibly one or more passive elements, or components, such as a capacitor, for example a bypass capacitor, or a protective diode, also encapsulated in the cavity, and possibly electrically connected to the support and/or to the cover.

The material of the support and/or of the cover may be, or may comprise at least one of, doped semiconductor material, for example silicon, the resistivity of which is between approximately 0.5 mOhm.cm and 20 mOhm.cm (or, more generally, the resistivity of which is suitable for the envisaged application) and/or metal.

The active element may be securely attached to the support through at least one dielectric layer positioned between the support and the active element, and between the support and the cover. Such a dielectric layer enables electrical insulation to be provided between the active element and the support, along with electric insulation between the support and the cover which are electrically conductive.

In this case, the first electrical connection may include at least one first portion of electrically conductive material in contact with the support and positioned at least in one aperture, or hole, formed through the dielectric layer, and/or in which the second electrical connection may include at least one second portion of electrically conductive material, electrically connected to the cover and positioned on the dielectric layer. The first portion of electrically conductive material may be connected electrically to the active element by at least one electric wire.

The second portion of electrically conductive material may be in electrical contact with an electrically conductive sealing bead, which may for example be metal, providing hermetic secure attachment of the cover to the support.

The active element may be securely attached to the support by microterminals (for example microbeads of fusible material, electrically conductive micropillars, etc.) also providing an electrical connection between the active element and the support and/or electrical connection between the active element and the cover), or the active element may be bonded on the dielectric layer and the first and/or the second electrical connection may include at least one electric wire.

The cover may include an electrically conductive substrate attached hermetically to the support, or the cover may include at least one electrically conductive thin layer. Such an electrically conductive thin layer may be between approximately 1 μm and 10 μm thick, or between approximately 1 μm and 5 μm thick, or more generally be less than approximately 10 μm thick.

The component may also include, when this cover includes an electrically conductive thin layer, for example comprising a preferably biocompatible metallic material, at least one thin dielectric layer positioned against the electrically conductive thin layer of the cover and between the support and the electrically conductive thin layer of the cover, where the second electrical connection is able to come through the thin dielectric layer via at least one aperture. By this means, the thin dielectric layer in this case provides electrical insulation between the support and the metal cover.

The component may include several active elements which are encapsulated hermetically and individually in cavities formed between the support, and several covers which are electrically insulated from one another, where each of the active elements is able to be connected electrically to one of the covers and to the support. The component may also include one or more passive elements, for example resistors, capacitors or inductors, electrically connected to the cover and/or to the support in the same manner as the active elements.

The component may include several active elements which are encapsulated hermetically and individually in cavities formed between the cover, or the covers, and several supports which are electrically insulated from one another, where each of the active elements is electrically connected to one of the electrically conductive supports and to the cover, or to one of the covers.

The support and the cover may be coated in a biocompatible material, for example silicon, parylene, an epoxy resin, silicon oxide, tantalum oxide and/or titanium oxide, produced for example in the form of a thin layer produced by atomic deposition (ALD).

Another embodiment relates to a medical device which is implantable, or which is able to be implanted, in a body, or at least a part of a body, whether human or animal, including at least one component as defined above.

A method for producing a component is also proposed including at least the following steps:
- production of at least one active element,
- production of a first electrical connection between the active element and at least one support and of a second electrical connection, separate from the first electrical connection, between the active element and at least one cover,
- hermetic encapsulation of the active element in at least one cavity formed between the support and the cover, in which the support and the cover are made from an electrically conductive material and are electrically insulated from one another.

It is also proposed a method for producing a component including at least the following steps:
- production of at least one active element,
- production of a first electrical connection between the active element and at least one support and of a second electrical connection, separate from the first electrical connection, between the active element and at least one cover,
- hermetic encapsulation of the active element in at least one cavity formed between the support and the cover, and in which:
- the support and the cover are made from an electrically conductive material and are electrically insulated from one another;
- the active element is securely attached to the support through at least one dielectric layer positioned between the support and the active element, and between the support and the cover;
- the second electrical connection includes at least one second portion of electrically conductive material electrically connected to the cover, positioned on the dielectric layer and electrically in contact with an electrically conductive sealing bead providing hermetic secure attachment of the cover to the support.

The support and the cover may be securely attached to one another by wafer bonding with plasma activation. In this case, the support and the cover form part of two substrates which are securely attached to one another, where the encapsulation of the active element is therefore accomplished at the scale of the wafers, or of the substrates. This technique is advantageous since the secure attachment is then accomplished at low temperature and is biocompatible.

BRIEF DESCRIPTION OF THE ILLUSTRATIONS

The present invention will be better understood on reading the description of example embodiments given purely as an indication and in no way restrictively, making reference to the appended illustrations in which:

FIGS. 1A to 6 and 8 represent components according to different embodiments,

Identical, similar or equivalent parts of the various figures described below have the same numerical references, to make it easier to move from one figure to another.

The various parts represented in the figures are not necessarily represented at a uniform scale, in order to make the figures more readable.

The various possibilities (variants and embodiments) must be understood as not being mutually exclusive, and being able to be combined with one another.

DETAILED ACCOUNT OF PARTICULAR EMBODIMENTS

Figure 1A:
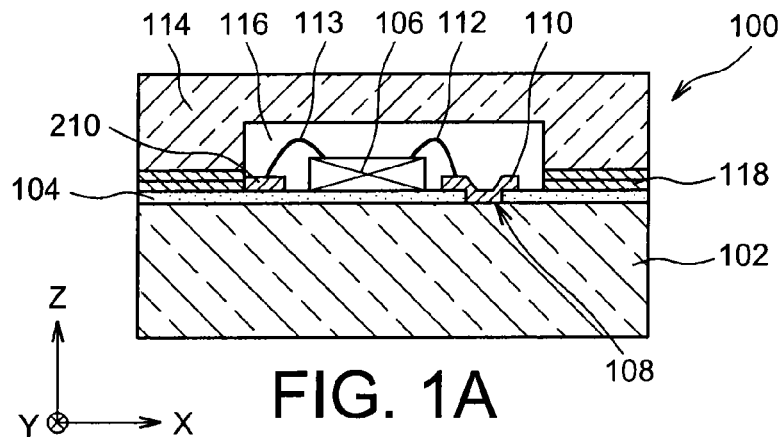
Figure 1B:
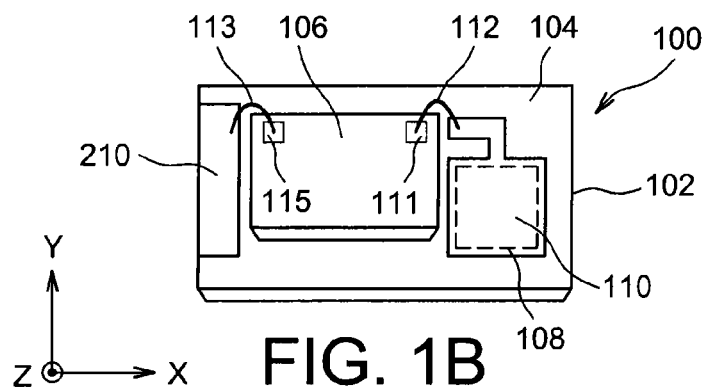

Reference is made firstly to FIGS. 1A and 1B, which represent respectively a section profile view and a top view of a component 100 according to a first embodiment.

Component 100 includes a support 102 comprising a highly doped semiconductor, in this case silicon, i.e. such that support 102 is electrically conductive. Support 102 is in this case a substrate. The doping may be of the N or P type, and such that the semiconductor of support 102 has low resistivity, for example of between approximately 0.5 mΩ.cm and 20 mΩ.cm. A P- or N-type resistivity of 0.5 mΩ.cm may be obtained by doping at approximately $2.10^{20}$ at/cm$^3$. A P-type resistivity of 20 mΩ.cm may be obtained for example by doping at approximately $3.10^{18}$ at/cm$^3$. Lastly, an N-type resistivity of 20 mΩ.cm may be obtained for example by doping at approximately $1.10^{18}$ at/cm$^3$.

In this first embodiment, the thickness (dimension along Z axis) of support 102 is, for example, between approximately 50 μm and 500 μm, or greater than approximately 50 μm, its length (dimension along X axis) is between approximately 0.5 mm and 10 mm, and its width (dimension along Y axis) is between approximately 0.5 mm and 5 mm.

The front face of support 102 is covered by a dielectric layer 104. Dielectric layer 104 is in this case a passivation layer of the organic or mineral type, for example comprising SiN and/or SiO$_2$ and/or SiON, and which is between approximately 100 nm and 5 μm thick.

An active element 106, for example a sensor, MEMS or NEMS, or again an integrated electronic circuit of the ASIC or FPGA type, is securely attached to dielectric layer 104. Dielectric layer 104 provides electrical insulation between active element 106 and support 102 which is electrically conductive due to doping. In the first embodiment represented in FIGS. 1A and 1B, active element 106 is bonded against dielectric layer 104.

Dielectric layer 104 includes an aperture 108, or hole, forming a means of access to support 102 from the side where dielectric layer 104 and active element 106 are located. A portion of electrically conductive material 110, for example comprising metal, is positioned in this aperture 108. An electric wire 112, for example comprising gold, electrically connects active element 106 to portion of electrically conductive material 110. By this means, active element 106 is electrically connected, via at least one electrical connection terminal 111 present on the front face of active element 106, i.e. the face of active element 106 opposite the one in contact with dielectric layer 104, to support 102 by a first electrical connection formed by portion 110 and electric wire 112. Portion 110 is produced such that it enables a satisfactory ohmic contact to be provided with support 102, and an electrical connection to be made (for example a weld) with electric wire 112. To this end, portion 110 comprises for example Ti and/or WN and/or Ni and/or Al and/or Cu and/or Au, and in this case is between approximately 100 nm and 5 μm thick.

A cover 114, in this case formed by a semiconductor substrate, such as doped silicon, is securely attached to support 102, forming a hermetic cavity 116 in which active element 106 is encapsulated. One or more passive components, such as a bypass capacitor or a protective diode, can also be produced and encapsulated in cavity 116. This cavity 116 is partly formed by etching in cover 114. The hermetic secure attachment of cover 114 to support 102 is accomplished by a sealing bead 118 comprising an electrically conductive material, for example gold, or a gold-based biocompatible alloy, formed on dielectric layer 104. This sealing bead 118 is, for example, obtained by thermocompression between at least one metal portion formed beforehand on dielectric layer 104 (for example derived from the same layer of material as the one used to produce portion 110) and at least one metal portion formed on the face of cover 114 intended to be positioned on the side of support 102, on the periphery of cavity 116. Sealing bead 118 can also be obtained by interdiffusion of a bead comprising gold with the semiconductor of the cover.

A second electrical connection, separate from the first electrical connection, connects active element 106 electrically with cover 114. To this end, a second electric wire 113 connects active element 106, via at least one other connection terminal 115 present on the front face of active element 106 to which electric wire 113 is connected, to a second portion of electrically conductive material 210, for example of a similar nature to the material of portion 110, produced on dielectric layer 104, next to active element 106. This second portion of electrically conductive material 210 is in electrical contact with sealing bead 118 which is electrically conductive. And, given that sealing bead 118 is also in electrical contact with cover 114, active element 106 is therefore indeed electrically connected to cover 114.

Thus, with component 100, active element 106 is electrically accessible, for example to send to active element 106 control signals and/or to receive output signals delivered by active element 106, via support 102 and cover 114, which are made of electrically conductive materials. Active element 106 therefore includes two electrical connections which are independently accessible through cover 114 and support 102, which are made from electrically conductive materials. These electrical means of access to active element 106 can be made firstly from the rear face of support 102 and/or from the lateral faces (those in planes parallel to plane (Y, Z)) of support 102, and secondly from the front face of cover 114 and/or from the lateral faces of cover 114. The electrical insulation between support 102 and cover 114 is provided by dielectric layer 104.

In order to reduce access resistance to support 102 as far as possible, the dimensions of aperture 108 are maximised in order to provide a large contact area between portion of electrically conductive material 110 and support 102. This contact area is advantageously such that the access resistance to the support is less than approximately 1 Ohm, and for example between approximately 0.05 mm$^2$ and 5 mm$^2$.

Similarly, in order to reduce access resistance to cover 114 as far as possible, the dimensions of the contact area between portion 210 and sealing bead 118 can be maximised, as with the contact surface between portion 110 and support 102 of component 100.

Figure 2:
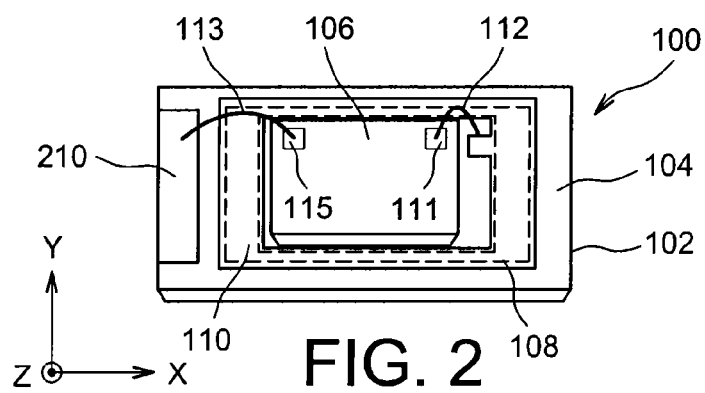

In the first embodiment represented in FIGS. 1A and 1B, aperture 108, and therefore the part of portion 110 in contact with support 102, is rectangular in shape (FIG. 1B is a top view of component 100 without cover 114 or sealing bead 118 present). In addition, aperture 108 is produced next to active element 106. In a variant represented in FIG. 2, aperture 108 is produced in the form of a channel surrounding active element 106, where portion of electrically conductive material 110 is positioned at least partly in aperture 108, around active element 106.

In a second embodiment it is possible to produce a portion 110 such that it is directly connected to active element 106, without having to use an electric wire. In this case, element 106 is for example transferred by flip-chip (securely attached by microbeads) on to platings which are electrically connected to portions of electrically conductive material 110 and 210.

Figure 3A:
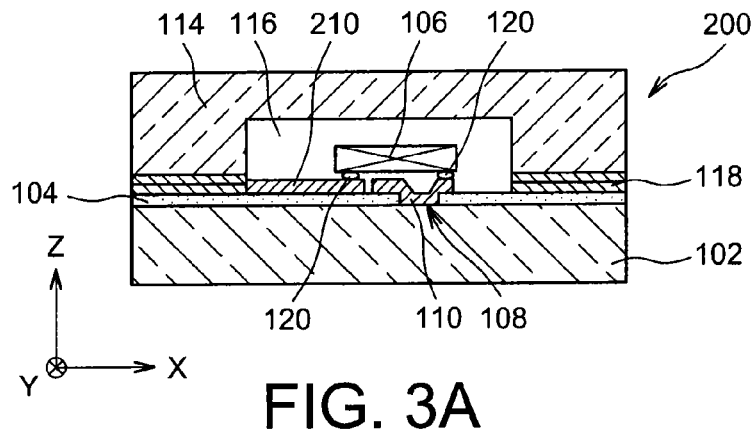
Figure 3B:
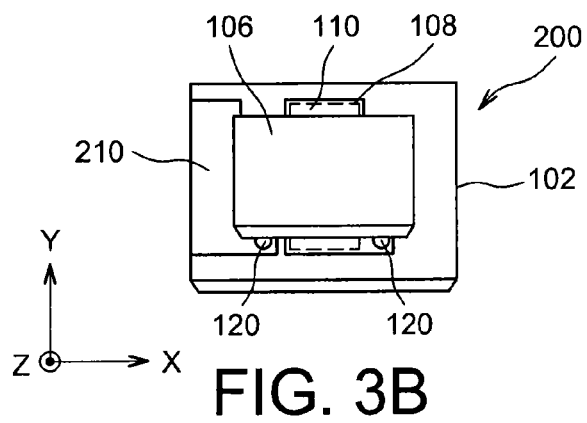

FIGS. 3A and 3B represent a component 200 according to a second embodiment. As with previously described component 100, component 200 includes electrically connected support 102, dielectric layer 104, active element 106, aperture 108 produced through dielectric layer 104, portion of electrically conductive material 110, electrically conductive cover 114, sealing bead 118 and electrically conductive portion 210. However, active element 106 is in this case welded directly, by its front face, which includes at least two electrical contact terminals, to portions of metal material, including portions 110 and 210, by "flip-chip", i.e. via microterminals 120 of micrometric or nanometric dimensions, and for example comprising at least one fusible material. These microterminals 120 can be microbeads, pillars comprising copper, micro-inserts or again any type of microelement comprising, for example, fusible material. In the example represented in FIGS. 3A and 3B, a single one of microterminals 120 is electrically connected to portion of electrically conductive material 110 which is positioned under active element 106 (where aperture 108 is in this case produced under active element 106), and where this microterminal 120 provides an electrical connection and a part of the mechanical connection between active element 106 and support 102 via portion 110. Another microterminal 120 is electrically connected to portion of electrically conductive material 210, and therefore provides, with portion 210 and sealing bead 118, the electrical connection between active element 106 and electrically conductive cover 114. Other microterminals, not represented in FIGS. 3A and 3B, provide the remainder of the mechanical connection between active element 106 and support 102 via portions of metal material, for example of similar nature to the material of portions 110 and 210, produced on dielectric layer 104 (where dielectric layer 104 electrically insulates these metal portions of support 102).

In this second embodiment, aperture 108 is not necessarily produced under the location of active element 106. It is, indeed, possible for aperture 108 to be produced next to and/or around active element 106, as in the previously described examples of FIGS. 1A, 1B and 2. In this case a part of portion 110 partly extends under active element 106 in order that at least one of microterminals 120 is able to be securely attached to this part of portion 110 and by this means electrically connect active element 106 to support 102.

Figure 4:
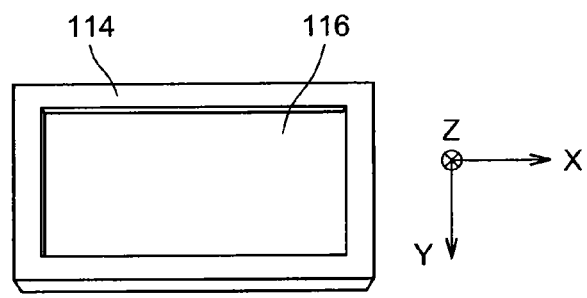

FIG. 4 represents a view from beneath of electrically conductive cover 114.

FIG. 5 represents a component 300 according to a third embodiment, including several active elements 106 produced on a single support 102, and encapsulated in mutually independent cavities 116. Active elements 106 of component 300 are, for example, similar to active element 106 of previously described component 200, i.e. securely attached to support 102 via microterminals 120 providing a first electrical connection to support 102 (where this connection is common for all active elements 106 due to the fact that the entire substrate forming support 102 is electrically conductive) and a second electrical connection to each electrically conductive cover 114 associated with each of active elements 106.

Covers 114 are produced such that they are electrically insulated from one another, by this means providing independence of the electrical connections between covers 114 and encapsulated active elements 106.

FIG. 6 represents a component 400 according to a fourth embodiment, including several active elements 106 encapsulated in mutually independent cavities 116. Compared to previously described component 300, active elements 106 are produced on supports 102 which are electrically insulated from one another (where this insulation is, for example, obtained by etching channels 402 in a substrate, forming supports 102, where channels 402 also come through dielectric layer 104 and sealing bead 118). By this means, the electrical connections produced between each active element 106 and support 102 to which associated active element 106 is securely attached are independent from one another. In addition, unlike previously described component 300, cavities 116 in which active elements 106 are encapsulated are formed by a single cover 114 (where cavities 116 are, for example, etched in a single substrate forming cover 114), attached hermetically to various supports 102 (where the etching of channels 402 may be accomplished after having securely attached cover 206 to the unetched initial substrate on which active elements 106 are produced). The electrical connections produced between active elements 106 and cover 114 are not insulated from one another.

In a variant of the two previous embodiments, it is also conceivable that all the electrical connections, between active elements 106 and cover 114, and active elements 106 and substrate 102, are independent.

In previously described components 300 and 400, active elements 106 are securely attached to support(s) 102 by flip-chip, via microbeads 120. As a variant, it is possible for active elements 106 to be securely attached to support(s) 102, for example by bonding on to dielectric layer 104, as with previously described component 100. In this case, the electrical connections, between the active elements and the cover, and/or the electrical connections between the active elements and the support, can be produced by electric wires, as previously described. Components 300 and 400 can be made biocompatible as previously described for components 100 and 200.

In all the previously described embodiments, the electrical connection between active element 106 and support 102 is provided by a portion of electrically conductive material 110 directly in contact with support 102 in aperture 108 formed through dielectric layer 104. In order to improve the ohmic contact between support 102 and portion of electrically conductive material 110, a doping may be applied locally by ionic implantation in support 102, in aperture 108, where portion of electrically conductive material 110 is in this case in direct contact with this doped area of support 102. Depending on the type of ionic implantation applied (N or P, and which is of the same type as that of support 102), it enables the ohmic contact between support 102 and electrically conductive portion 110 to be improved. Such an ionic implantation can also be applied in the cover in the area of the contact areas with the sealing bead securely attaching the cover to the support. By this means the ohmic contact between the cover and the sealing bead is improved, and therefore the quality of the electrical connection between the cover and the active element or elements.

When the component is produced, after the deposition of the material of portion 100 in aperture 108, a thermal treatment can be applied, forming, in the interface between portion 110 and support 102, a portion of silicide improving still further the electrical contact between support 102 and portion of electrically conductive material 110.

A description is now given, in connection with FIGS. 7A to 7H, of a method for producing a component 500 according to a fifth embodiment. Although the production of a single component 500 is described in connection with these figures, these steps can be steps for collective production of several components, where the substrates used can be used to form the covers and the supports of several components. The different active elements are then encapsulated collectively in independent cavities, and the substrates are then divided in order to make the produced components independent.

Figure 7A:
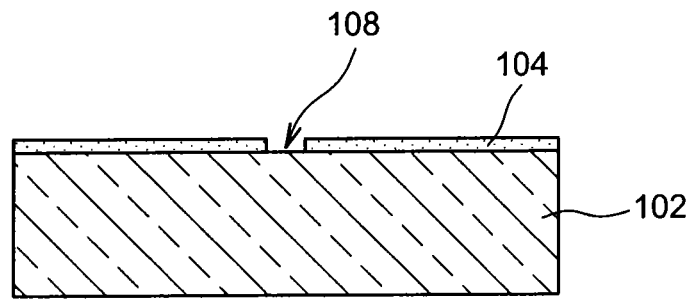
FIGS. 7A to 7H represent the steps of a method to produce a component according to a particular embodiment.

In a first step, a front face of support 102, which is a highly doped semiconductor substrate (resistivity, for example, of between approximately 0.5 mOhm.cm and 20 mOhm.cm), of type N or P, is covered with a passivation layer corresponding to dielectric layer 104. Depending on the nature of the material of dielectric layer 104, which comprises for example $SiO_2$, SiN or SiON, this layer is for example produced via thermal oxidation or a deposition on the front face of support 102. An aperture 108, intended to form an area of access to support 102 for the future electrical connection of the active element, is then produced through dielectric layer 104, for example by implementing steps of photolithography and etching (FIG. 7A).

Figure 7B:
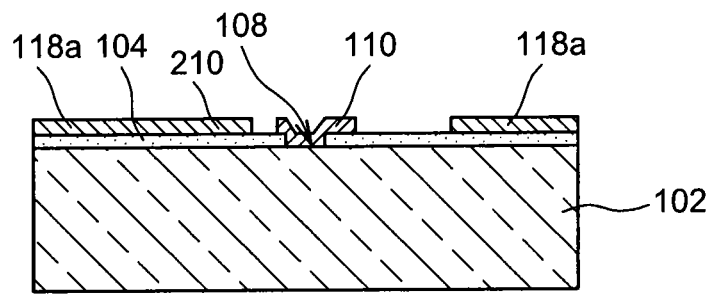

As represented in FIG. 7B, a layer of electrically conductive material, in this case metal such as gold or an alloy of gold and tin, is deposited on dielectric layer 104 (directly or on to a possible primer layer and/or a possible barrier layer) and in aperture 108, in order to obtain an ohmic contact between support 102 and this electrically conductive layer.

This layer is, for example, produced by means of electrolytic deposition, plasma deposition (for example of the PECVD type, i.e. Plasma-Enhanced Chemical Vapour Deposition), or again deposition by evaporation or by PVD (Physical Vapour Deposition). This layer is then structured by etching in order to form portions of electrically conductive material 110 and 210 intended to electrically connect the active element to support 102 and to cover 114, and also to a part 118a of sealing bead 118. As a variant, the sealing bead can be produced independently of portions of electrically conductive material 110, 210, by means of the implementation of separate steps of the deposition and etching, for example when part 118a of sealing bead 118 comprises a different material and/or is of a thickness different to electrically conductive portions 110, 210 to be produced. Similarly, when the biocompatible component includes metal docking terminals for cables or fusible microbeads, these elements can be produced independently from portion 110 and from part 208a of sealing bead 208.

To improve ohmic contact between portion 110 and support 102 a thermal treatment can be implemented enabling metal species (originating from portion 110) to be diffused in support 102, in aperture 108, thus forming a silicide in the area of the contact with portion 110.

Figure 7C:
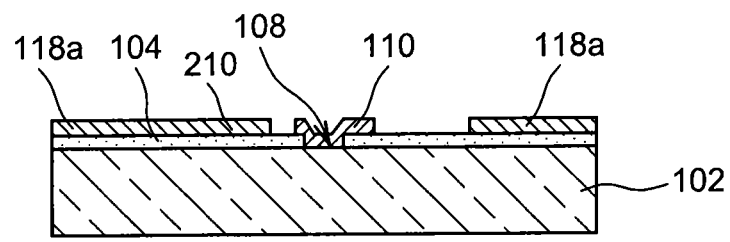

When support 102 is too thick, it may be thinned, for example by means of grinding and/or chemical mechanical polishing of its rear face, i.e. the face opposite the one where dielectric layer 104 is located (see FIG. 7C).

Figure 7D:
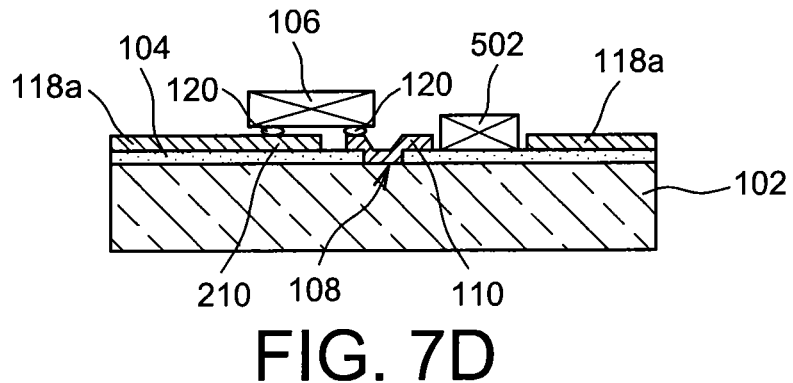

The different electronic elements (for example, active elements such as electronic circuits and/or NEMS or MEMS, and/or passive components) of biocompatible component 500 are then transferred to support 102. In the example of FIG. 7D, active element 106 is securely attached by flip-chip, via microterminals 114 (in this case microbeads), to the metal portions formed on support 102. One of microbeads 120 is electrically connected to metal portion 110, thus providing the electrical connection between active element 106 and support 102, and at least one other of microbeads 120 is electrically connected to portion 210 which is merged with part 118a of the sealing bead, providing the electrical connection between active element 106 and sealing bead 118 which will be used to securely attach cover 114 made of electrically conductive material to support 102. A passive element 502 is also transferred to support 102, by means of bonding on dielectric layer 104.

Figure 7E:
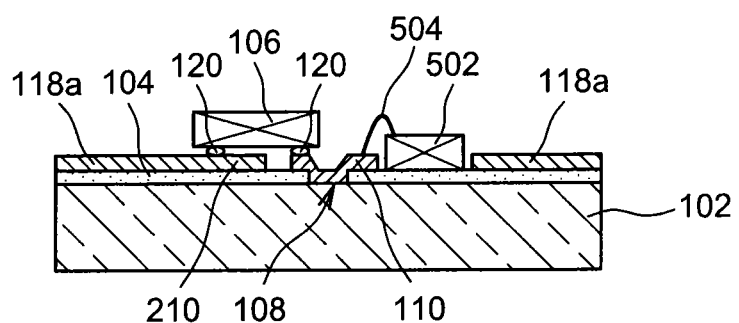

Any wire bondings of the elements previously transferred on to support 102 are then made. In FIG. 7E, element 502 is electrically connected to portion 110 by a wire 504 (the other wire bondings connected to element 502 are not represented).

Simultaneously with the steps previously described in connection with FIGS. 7A to 7E, cover 114, intended to be transferred to support 102, is prepared.

Figure 7F:
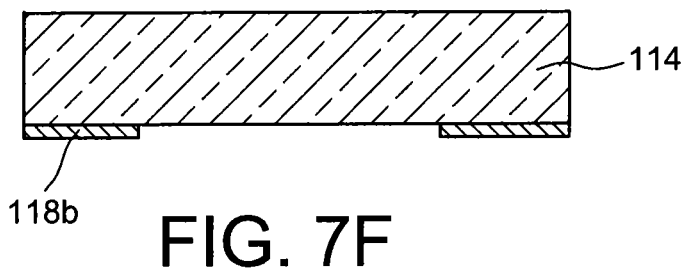

To this end, a deposition and a structuring of a metal layer are firstly accomplished, where the layer comprises, for example, gold or an alloy of gold and tin, on a highly doped semiconductor substrate (such that it is electrically conductive), such that remaining portions 118b of the metal layer are intended to form a part of sealing bead 118 (FIG. 7F). The metal layer can be formed by electrolytic means, by plasma deposition or by deposition by evaporation. A thermal treatment can also be implemented in order to diffuse in cover 114 metal species originating from portions 118b, and by this means to improve ohmic contact between cover 114 and these portions 118b.

Figure 7G:
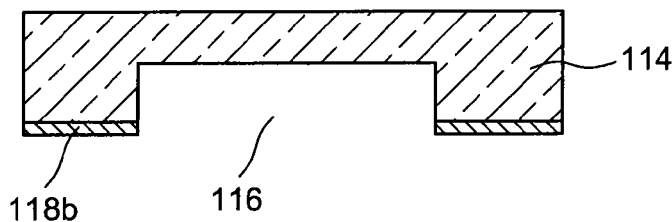

The substrate forming cover 114 is then etched to form cavity 116 in which the electrical elements (active element 106 and passive element 502) of component 500 will be encapsulated (FIG. 7G). Cavity 116 is made, for example, by chemical etching from a solution of the KOH or TMAH type, or advantageously by plasma etching of the DRIE (Deep Reactive Ionic Etching) type, enabling sides of cavity 116 to be obtained which are correctly perpendicular relative to the main faces of the substrate from which cover 114 is produced. Depending on the depth of cavity 116, etching of cover 114 is accomplished through a photosensitive resin mask and/or a hard mask, for example one made of silicon oxide.

Figure 7H:
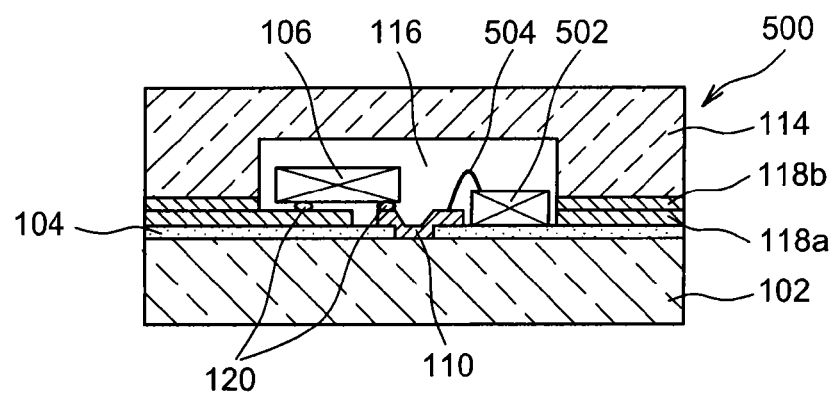

Lastly, as represented in FIG. 7H, cover 114 is securely attached to support 102 by means of an attachment, produced for example by melting or thermocompression, of portions 118a with portions 118b, forming sealing bead 118. This attachment can be accomplished at the wafer scale, simultaneously forming several biocompatible components by means of collective encapsulation of the elements produced on support 102, or at the chip scale, i.e. by attaching only cover 114 of component 500 to support 102. In the case of a collective encapsulation forming several biocompatible components, the substrates used to form the cover or covers and the support or supports can be divided to obtain the independent biocompatible devices.

In the previously described examples, cover 114 is a substrate which has been transferred and attached to the support. As a variant, the component's cover may be one or more thin layers. To accomplish this, when the component's active element is encapsulated, instead of transferring to the support a substrate in which the cavity has been etched, a sacrificial layer comprising a material able to be etched selectively compared to the other materials which will be present in the cavity (materials of the cover, the active element, dielectric layer 104, etc.) is deposited on support 102. This sacrificial layer is structured such that the remaining portion (or the remaining portions in the case of a collective encapsulation of several active elements in different cavities), the thickness of which is, for example, of between approximately 1 µm and 100 µm, is the volume of the cavity to be produced to incorporate the active/passive element or elements. One or more thin layers (the thickness of which is, for example, between approximately 1 µm and 5 µm), for example comprising $SiO_2$ and/or SiN, are then deposited, covering the support (notably the dielectric layer covering the support) and the remaining portion of the sacrificial layer. One or more apertures, the diameter of which can be between approximately 1 µm and 10 µm, are then produced through the thin layers, forming by this means one or more means of access to the portion of sacrificial material. The portion of sacrificial material is then eliminated by etching through the previously produced apertures. The dielectric thin layer or layers is/are then covered by one or more electrically conductive thin layers, advantageously comprising metal, and of thickness of between approximately 1 µm and 10 µm, thus forming the cover made of electrically conductive material and sealing the apertures previously produced in the dielectric thin layer or layers. As with the previously described example embodiments, the active element is electrically connected to the support and to the cover.

Figure 8:
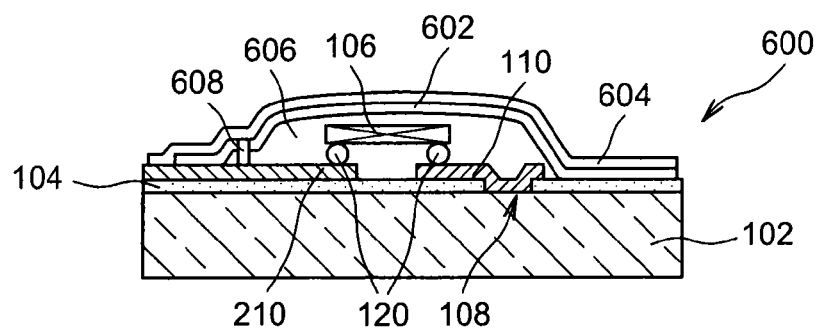

An example embodiment of such a biocompatible component 600, including a cover formed by a thin layer, is represented in FIG. 8. In this example, a first dielectric thin layer 602, the thickness of which is between approximately 1 µm and 5 µm, and comprising $SiO_2$ and/or SiN, forms the inner upper wall of cavity 606 in which active element 106 is encapsulated. In this case the cover is an electrically conductive thin layer 604, the thickness of which is between approximately 1µ and 10 µm, and comprising for example metal such as Cu and/or Ni and/or Al and/or Au, covering dielectric thin layer 602.

Active element 106 (the thickness of which is advantageously less than or equal to approximately 50 µm, such that it can be encapsulated by a thin layer) is securely attached to support 102 (which is covered by dielectric layer 104) by microterminals 102, at least one of which is securely attached to portion of electrically conductive material 110 electrically connected to support 102. At least one other of microbeads 102 is securely attached to portion of electrically conductive material 210 which is electrically connected to cover 604 via another portion of electrically conductive material 608 which forms a conductive metal link between portion 201 and cover 604, coming through dielectric thin layer 602, at the edge of cavity 606 in order that this link causes no obstruction for the elements present in cavity 606.

The component described in the various embodiments can apply to all systems requiring encapsulation, for example vacuum encapsulation, of an active element, such as for example in the field of MEMS/NEMS (Micro/Nano-Electro-Mechanical Systems), for example resonators or switches, MOEMS (Micro-Opto-Electro-Mechanical Systems) or again infrared detectors such as uncooled bolometers.

The component is advantageously used for production of a medical device which is implantable in a body, or a part of a body, whether human or animal.

Figure 9:
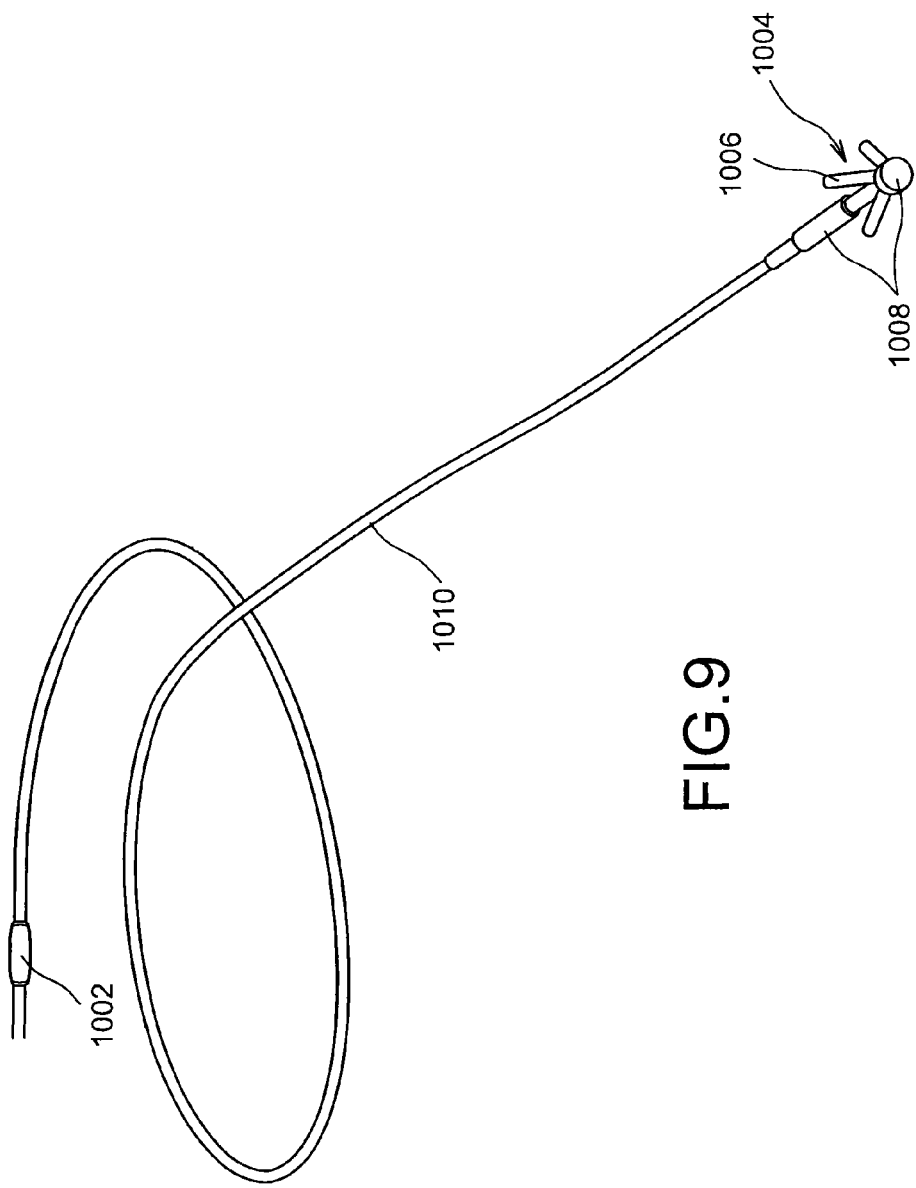
FIG. 9 represents an example of an implantable medical device according to a particular embodiment.

An example of such a medical device 1000 is for example represented in FIG. 9. In this example, medical device 1000 is a cardiac stimulation probe. It includes a first end where a connector 1002 is positioned, and a second end where a biocompatible component 1004 as previously described is positioned. An attachment mechanism 1006 and electrodes 1008 are also present at this second end. A body comprising a conductive material coated in a biocompatible insulating material connects both ends of probe 1000. In such a probe, the active element of component 1004 can be a blood pressure sensor (for example of the flexible membrane type with strain gauges or with variable capacity), or again an accelerometer (for example, a piezoelectric or MEMS-type accelerometer) intended to measure endocardial acceleration. The electrical connections of the component's cover and support are directly or indirectly connected to microcables or microwires, which are themselves connected to both ends of probe 1000. In such a probe the cover is for example electrically connected to the proximal electrode and the support is for example connected to the distal electrode, or vice versa.

The invention claimed is:

1. A component including at least one active element hermetically encapsulated in at least one cavity formed between at least one support and at least one cover, in which the support and the cover are made from at least one electrically conductive material, and are insulated electrically from one another, and include a first electrical connection between the active element and the support, and a second electrical connection, separate from the first electrical connection, between the active element and the cover, and in which:
   - the active element is securely attached to the support through at least one dielectric layer positioned between the support and the active element, and between the support and the cover;
   - the second electrical connection includes at least one second portion of electrically conductive material electrically connected to the cover, positioned on the dielectric layer and electrically in contact with an electrically conductive sealing bead providing hermetic secure attachment of the cover to the support.

2. The component according to claim 1, in which the active element includes at least one of an integrated electronic circuit, a device of the MEMS/NEMS type and a sensor measuring at least one physiological parameter.

3. The component according to claim 1, in which the material of the support and of the cover comprises at least one of doped semiconductor, the resistivity of which is between approximately 0.5 mOhm.cm and 20 mOhm.cm, and metal.

4. The component according to claim 1, in which the first electrical connection includes at least a first portion of electrically conductive material in contact with the support and positioned at least in one aperture formed through the dielectric layer.

5. The component according to claim 1, in which the active element is attached to the support by microterminals, also providing the electrical connection between the active element and the support and/or the electrical connection between the active element and the cover, or in which the active element is bonded on the dielectric layer and the first and/or the second electrical connection includes at least one electric wire.

6. The component according to claim 1, in which the cover includes an electrically conductive substrate attached hermetically to the support, or in which the cover includes at least one electrically conductive thin layer.

7. The component according to claim 6, also including, when the cover includes an electrically conductive thin layer, at least one dielectric thin layer positioned against the electrically conductive thin layer of the cover and between the support and the electrically conductive thin layer of the cover, and in which the second electrical connection comes through the dielectric thin layer via at least one aperture.

8. The component according to claim 1, including several active elements which are encapsulated hermetically and individually in cavities formed between the support, and several covers which are electrically insulated from one another, where each of the active elements is connected electrically to one of the covers and to the support.

9. The component according to claim 1, including several active elements which are encapsulated hermetically and individually in cavities formed between the cover, or the covers, and several supports, which are electrically insulated from one another, where each of the active elements is connected electrically to one of the supports and to the cover or to one of the covers.

10. The component according to claim 1, in which the support and the cover are coated in a biocompatible material such that the component is biocompatible and able to be implanted in a body, or at least a part of a body, whether human or animal.

11. A medical device which is implantable in a body, or at least a part of a body, whether human or animal, including at least one component according to claim 10.

* * * * *